United States Patent [19]

Rosenberger

[11] 4,311,645
[45] Jan. 19, 1982

[54] SYNTHESIS OF SRS-ACTIVE COMPOUNDS

[75] Inventor: Michael Rosenberger, Caldwell, N.J.

[73] Assignee: Hoffmann-La Roche Inc., Nutley, N.J.

[21] Appl. No.: 133,180

[22] Filed: Mar. 24, 1980

[51] Int. Cl.$^3$ .................. C07D 303/42; C07D 303/38
[52] U.S. Cl. ............................. 260/348.61; 546/184; 560/153; 562/557; 568/59; 568/448; 568/597; 568/873; 549/80
[58] Field of Search ................................. 260/348.61

[56] References Cited

U.S. PATENT DOCUMENTS 3,882,148  5/1975  Augstein et al. ............... 260/345.2
4,174,402 11/1979  Mielens ........................... 424/274

OTHER PUBLICATIONS

M. Hitchcock, Jour. Pharm. and Experimental Therapeutics, vol. 207, No. 2, (1978) pp. 630–640.
S. Hammarstrom et al., Biochemical and Biophysical Communications, vol. 91, No. 4 (1979), pp. 1266–1272.
Jeffrey L. Fox, Science, vol. 57 (1979) p. 19.
E. J. Corey et al., Jour. Am. Chem. Soc., Oct. 24, 1979, vol. 101, No. 22, pp. 6748–6749.
Michael Rosenberger et al., J. Am. Chem. Soc., vol. 102, p. 5425 (1980).

*Primary Examiner*—Norma S. Milestone
*Attorney, Agent, or Firm*—Jon S. Saxe; George M. Gould; William H. Epstein

[57] ABSTRACT

A chemical synthesis of an SRS-A active compound from the reaction product of 1-halo-2-octyne and the ether of 2-penten-4-yn-1-ol including intermediates in the synthesis, some of which being antagonists of SRS-A useful for treating allergic reactions.

2

SYNTHESIS OF SRS-ACTIVE COMPOUNDS

BACKGROUND OF INVENTION

The material SRS-A (slow reacting substance of anaphylaxis) like histamine is released from cells of mammals during an allergic reaction. The SRS-A excreted by the cells contracts smooth muscle tissue producing such effects as asthmatic attacks. Thus there has been a great need for drugs which would specifically antagonize the effects of SRS-A released by the cells of man during an allergic response.

Conventional anti-allergic drugs such as anti-histamines, while effective in neutralizing the histamine produced during an allergic response, have been ineffective in neutralizing or antagonizing the effects of SRS-A. This has limited the usefulness of these antihistamines as anti-asthmatic agents. Therefore, it has long been desirable to develop drugs which will specifically antagonize the effects of SRS-A released during an allergic response.

In screening compounds for anti-SRS-A activity, natural SRS-A has been utilized. See Mielens, U.S. Pat. No. 4,174,402; Augstein et al., U.S. Pat. No. 3,882,148; Hitchcock, J. Pharmacol, Vol. 207, No. 6, page 630 (1978). A problem encountered with utilizing SRS-A obtained from natural sources in the many impurities which must be removed before the material can be used to determined the specific SRS-A antagonist effect of various compounds. SRS-A material from natural biological souces contains many difficult to separate impurities which interfere with the determination of whether a compound is specifically active against SRS-A. In some cases, a false positive may arise due to the activity of the compound to be tested against some component included within the natural SRS-A material and not SRS-A itself. To neutralize some of the contaminates such as acetyl choline and histamine present in biologically obtained SRS-A, various additives have been added to the naturally obtained SRS-A before testing. While these additives have to an extent neutralized these contaminates, residues of these contaminates may still be present which interfere with the assay. Furthermore, it has been desired to synthetically produce the active components in SRS-A to avoid such contaminates and produce a standard material. Such standard material would not contain contaminates which could interfere with the determination of the anti-SRS-A properties of a compound. Furthermore, a synthetically produced SRs-A active compound would avoid costly purification techniques not utilized in obtained natural SRS-A.

Recently the structure of SRS-A has been reported by Samuelsson et al., in *Chemical and Engl News*, June 11, 1979, p. 19 and in Science, 1979, Vol. 57, p. 19, who designates leukotriene C. having a structure as follows:

$$CH_3-CH_2-CH_2-CH_2-CH_2-\overset{\Delta}{CH=CH}-CH_2-\overset{\Delta}{CH=CH}-\overset{\Delta}{CH=CH}-\overset{\Delta'}{CH=CH}-CH-\underset{|}{CH}-CH_2-CH_2-CH_2COOH \quad \text{I-A}$$

(positions 20 through 1, with OH at position 5, $CO_2H$ branch at position 3, and $S-CH_2-CH(NH_2)$ substituent)

where $\Delta'$ indicates a trans configuration across the double bond and $\Delta$ a cis configuration across the double bond.

On the other hand, Corey et al. in *J. of Amer. Chemical society*, 101:6748 (1979) has identified the material obtained by Samuelsson as a 5S,6R compound of the structure:

$$CH_3-CH_2-CH_2-CH_2-CH_2-\overset{\Delta}{CH=CH}-CH_2-\overset{\Delta}{CH=CH}-\overset{\Delta'}{CH=CH}-\overset{\Delta'}{CH=CH}-CH-CH-(CH_2)_3COOH \quad \text{I-B}$$

(with OH, S–$CH_2$–CH(NH_2)–COOH substituent)

where $\Delta$ and $\Delta'$ are as above.

While the compound obtained by Samuelsson has been found to have SRS-A activity, Samuelsson and Corey et al. in Biochem Biophys Research Com. Vol. 91, No. 4, 1979, believe that SRS-A has a different structure, having gluthione in place of cysteine.

SUMMARY OF INVENTION

In accordance with this invention, we have discovered a new method for synthesizing SRS-A active compounds of the formula:

$$CH_3-CH_2-CH_2-CH_2-CH_2-\overset{\Delta}{CH=CH}-\overset{\Delta}{CH=CH}-\overset{\Delta'}{CH=CH}-\overset{\Delta'}{CH}-CH-CH_2-CH_2-CH_2-\overset{O}{\overset{\|}{C}}-OH \quad \text{I}$$

(with $S-CH_2-CH(NH_2)-CO_2H$ and OH substituents; positions 20 through 1)

where
$\Delta$ and $\Delta'$ is as above
as well as a SRS-A active compound of the formula $$CH_3-CH_2-CH_2-CH_2-CH_2-\underset{15}{C}\equiv\underset{14}{C}-\underset{13}{CH_2}-\underset{12}{C}\equiv\underset{11}{C}-\underset{10}{CH}=\underset{9}{CH}-\overset{\Delta'}{\underset{8}{C}}=\underset{7}{C}-\underset{6}{CH}-\underset{5}{\overset{\overset{\displaystyle S-CH_2-\overset{\overset{\displaystyle NH_2}{|}}{CH}-COOH}{|}}{CH}}-\underset{4}{CH_2}-\underset{3}{CH_2}-\underset{2}{CH_2}-\underset{1}{\overset{\overset{\displaystyle O}{\|}}{C}}-OH \quad\quad IV$$

$$\underset{20}{\phantom{CH_3}}\ \underset{19}{\phantom{CH_2}}\ \underset{18}{\phantom{CH_2}}\ \underset{17}{\phantom{CH_2}}\ \underset{16}{\phantom{CH_2}}\quad\quad\quad\quad\quad\quad\quad\quad\quad\quad\quad\quad\quad\quad\quad\quad\quad\underset{|}{OH}$$

wherein
Δ' is as above
and salts thereof. These material are prepared through the reaction of $$R-C\equiv C-CH_2-X \quad\quad II$$

wherein
R is $CH_3-CH_2-CH_2-CH_2-CH_2-$ and,
X is halogen
with a compound of the formula:

$$HC\equiv C-CH=CH-CH_2-OR_1 \quad\quad III$$

wherein
R₁ taken with its attached oxygen atom forms an ether protecting group which upon hydrolysis yields the hydroxy group.

In accordance with the process of this invention, the compounds formula I and IV can be produced with any stereo configuration such as cis or trans about the 9-10 double bond or as mixtures thereof. Furthermore, the compounds of formula I and IV can be produced as the 5S,6R isomer of formula I-B or as one of the other following isomers
5R,6S;
5S,6S; and
5R,6R
or mixtures of the above isomers.

As seen from the above, in accordance with this invention, new SRS-A active compounds such as the 5S,6S isomer of the compound of formula I having the formula:

$$\overset{\Delta}{R-CH=CH}-CH_2-\overset{\Delta}{CH=CH}-CH=CH-\overset{\Delta'}{CH=CH}-\overset{\overset{\displaystyle OH}{\blacktriangledown}}{CH}-\underset{\underset{\underset{NH_2\ \ O}{|\ \ \ \ \|}}{S-CH_2-CH-C-OH}}{\overset{\blacktriangle}{CH}}-(CH_2)_3-COOH \quad\quad I-C$$

wherein
R, Δ and Δ' are as above and its diastereomer, i.e. the 5R,6R isomer which has the formula:

$$\overset{\Delta}{R-CH=CH}-CH_2-\overset{\Delta}{CH=CH}-CH=CH-\overset{\Delta'}{CH=CH}-\overset{\overset{\displaystyle OH}{\equiv}}{\underset{\equiv}{CH}}-\underset{\underset{\underset{NH_2\ \ O}{|\ \ \ \ \|}}{S-CH_2-CH-C-OH}}{CH}-(CH_2)_2-COOH \quad\quad I-D$$

wherein

R, Δ and Δ' are as above can be prepared. Also, the salts of the compounds of formulae I-C and I-D can be prepared.

In accordance with this invention, the compounds of formula I and IV including their salts can be utilized for their SRS-A activity in determining the anti SRS-A activity of compounds. In fact, the compounds of formula I and IV have SRS-A activity equivalent to biologically obtained SRS-A.

In accordance with this invention, we have discovered that compounds of the formula $$R-C\equiv C-CH_2C\equiv C-CH=CH-CH=CH-\overset{\Delta'}{CH}-\underset{\underset{O}{\diagdown\diagup}}{CH}-CH_2-CH_2-CH_2-\overset{\overset{\displaystyle O}{\|}}{C}-OR_2 \quad\quad IV-A$$

wherein
R is as above; R₂ is lower alkyl and Δ' is as above, and salts thereof where R₂ is hydrogen are antagonists of SRS-A. Therefore, the compounds of formula IV-A is useful in the treatment of bronco-constriction.

DETAILED DESCRIPTION

The term "halogen" are used herein includes all four halogens, i.e. chlorine, fluorine, bromine and iodine with chlorine and bromine being preferred. When "R₁" taken together with its attached oxygen atom forms an ether group which upon hydrolysis yields the hydroxy group, the ether formed includes any conventional hydrolyzable ether. Among the preferred hydrolyzable ethers are included alpha-lower alkoxy-lower alkyl, tetrahydropyranyl, benzyl, benzhydryl, trityl, t-butyl and 4-methyl-5,6-dihydro-2H-pyranyl ethers. Among the lower alkoxy-lower alkyl ethers are methoxymethyl ether, alpha methoxy ethyl ether, alpha ethoxy ethyl ether, etc.

The term "lower alkyl" designates any alkyl group containing from 1 to 7 carbon atoms, such as methyl, ethyl, propyl, butyl, etc. The term "lower alkoxy" includes any lower alkoxy group containing from 1 to 7 carbon atoms, such as methoxy, ethoxy, isopropoxy, etc.

As used herein, the term "ester protecting group removable by hydrolysis" designates any conventional ester formed by esterifying the acid to be protected and which ester group can be removed to form the acid by conventional hydrolysis techniques. Any conventional ester that can be hydrolyzed to yield the acid can be utilized as a protecting group. Exemplary esters used for this purpose are lower alkyl esters, particularly methyl, and ethyl ester, aryl esters, particularly phenyl esters, and the aryl lower alkyl esters, particularly the benzyl ester.

As used herein the term "aryl" signifies mononuclear aromatic hydrocarbon groups such as phenyl which can be unsubstituted or substituted in one or more positions with a lower alkyl or nitro substituent and polynuclear aryl groups such as naphthyl, anthryl, which can be unsubstituted or substituted with one or more of the aforementioned groups. The preferred aryl group is the phenyl group.

In accordance with this invention, the compounds of formulae II and III are reacted to produce a compound of the formula:

$$R-C{\equiv}C-CH_2-C{\equiv}C-CH{=}CH-CH_2-OR_1 \quad V$$

wherein R and $R_1$ are as above.

In carrying out this reaction, the compound of the formula II is reacted via a Grignard reaction with the compound of formula III. Any of the conditions conventional in Grignard reactions can be utilized in carrying out this reaction.

The compound of formula V is converted to the compound of formula I via the following intermediates:

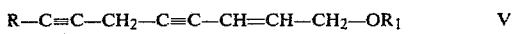

$$R-C{\equiv}C-CH_2-C{\equiv}C-CH{=}CH-CH_2OH \quad VI$$

$$R-C{\equiv}C-CH_2-C{\equiv}C-CH{=}CH-CHO \quad VII$$

atoms forms a hydrolyzable ester group; and $R_5$ and $R_6$ individually are lower alkyl containing from 1 to 2 carbon atoms or taken together with their attached sufur atom form a saturated 4 to 6 member heterocyclic ring with said attached sulfur atom as the only hetero atom; and $\Delta'$ is as above.

The compound of formula V is converted to the compound of formula VI by ether hydrolysis. Any conventional method of ether hydrolysis can be utilized to convert the compound of formula V to the compound of formula VI. Among the conventional methods for carrying out this hydrolysis is by treating the compound of formula V with an acid under aqueous conditions. Any conventional acid can be utilized to effect this hydrolysis. Of the preferred acids are included inorganic acids such as sulfuric acid, hydrochloric acid, etc. In carrying out this reaction, temperature and pressure are not critical and this reaction can be carried out at room temperature and atmospheric pressure. If desired, higher or lower temperatures can be utilized.

The compound of formula VI is converted to the compound of formula VII by treating the compound of formula VI with oxidizing agent. Any conventional oxidizing agent utilized to convert alcohols to aldehydes can be utilized. Among the preferred oxidizing agents are included silver salts such as silver carbonate, maganese dioxide, Jones reagent, chromate oxidizing agents, such as pyridinium dichromate, etc. Any of the conditions conventionally utilized with these oxidizing agents can be utilized in this conversion.

The compound of formula VII is converted to the compound of formula VIII by reacting the compound of formula VII with vinyl magnesium halide via a Grignard reaction. Any of the conditions conventionally utilized in Grignard reactions can be utilized in carrying out this conversion. The compound of formula VIII is converted to the compound of formula IX by

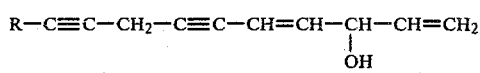 

 

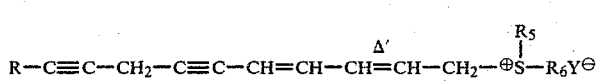 

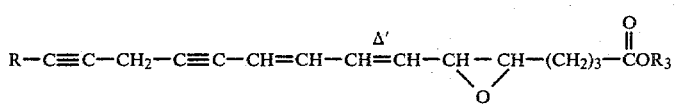 

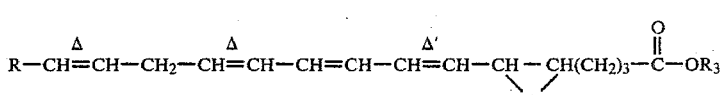 

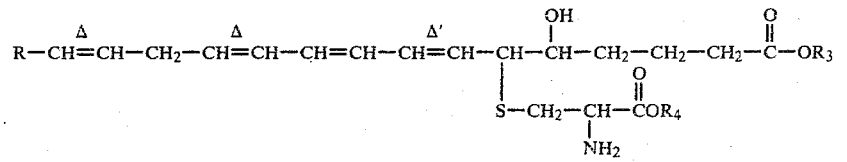

wherein
$\Delta$ designates a cis double bond; y is halogen; R is as above; $R_4$ is hydrogen or taken together with its attached oxygen atom forms a hydrolyzable ester group; $R_3$ taken together with its attached oxygen treating the compound of formula VIII with a halogenating agent. Any conventional halogenating agent can be utilized to carry out this reaction. Among the preferred halogenating agents are the phosphorous trihalides such as phosphorus tribromide, phosphorus trichloride, etc. Any of the conditions conventionally utilized with these halogenating agents can be utilized in carrying out this reaction. The halogenation causes rearrangement of the terminal double bond in the compound of formula VIII to produce a trans double bond in the compound of formula IX. This trans double bond is carried through the conversion of the compound of formula IX to the compound of formula I.

The compound of formula IX is converted to the salt of formula X by reacting the compound of formula IX with a sulfide of the formula $$R_5-S-R_6 \qquad XIV$$

wherein $R_5$ and $R_6$ are as above.

Among the compounds of formula XIV are included diethylsulfide, dimethylsulfide, tetrahydrothiophene, thietane and tetrahydrothiopyran. Generally, this reaction is carried out in an aqueous organic medium. As the organic solvent, there can be utilized any of the conventional water miscible organic solvents. Among the conventional solvents are included the lower alkanol solvents such as methanol, ethanol, isopropanol, etc., ether solvents such as tetrahydrofuran, etc. In carrying out this reaction, temperature and pressure are not critical and room temperature and atmospheric pressure are preferred. However, any temperature from 0° C. to 45° C. can be utilized.

The compound of formula X is converted to the compound of formula XI by reacting the compound of formula X with a compound of the formula $$\overset{O}{\underset{\|}{OCH-CH_2-CH_2-CH_2-C-OR_3}} \qquad XV$$

wherein $R_3$ is as above.

The compound of formula X is reacted with the compound of formula XV in the presence of a strong base. Any conventional strong base can be utilized to carry out this reaction. Among the preferred bases are the alkali metal bases such as sodium hydroxide, potassium hydroxide, lithium hydroxide, etc. Generally, any conventional strong inorganic base can be utilized in carrying out this reaction. This reaction is carried out in an aqueous medium. In carrying out this reaction, temperature and pressure are not critical and this reaction can be carried out at room temperature and atmospheric pressure. On the other hand, temperature of from $-30°$ to 45° C. can be utilized in carrying out this reaction.

If desired, the compound of formula XI can be separated into the cis and trans epoxide by conventional methods of separation. Any conventional methods of separation such as liquid chromatography can be utilized to effect this separation. Any of the conditions conventional in liquid chromatography can be utilized. On the other hand, the compound of formula XI can be utilized throughout the reaction as a mixture of the cis and trans epoxides.

The compound of formula XI either as a cis or trans epoxide or as mixtures thereof can be converted to the compound of formula XII by hydrogenation in the presence of a selective hydrogenation catalyst. Any conventional catalyst which selectively reduces only the triple bond (acetylene linkage) to a double bond can be utilized in carrying out this conversion. Among the preferred selective hydrogenation catalysts are the palladium catalysts which contain a deactivating material such as lead, lead oxide or sulfur. Among the preferred selective hydrogenation catalysts are included the palladium-lead catalyst of the type disclosed in Helvetica Chimica Acta.; 35 pg. 446 (1952) and U.S. Pat. No. 2,681,938—Lindlar. These catalysts are commonly known as Lindlar catalysts. In carrying out this hydrogenation, temperature is not critical and this reaction can be carried out at room temperature and atmospheric pressure. On the other hand, elevated or reduced temperatures can be utilized. Generally, this reaction is carried out in an inert organic solvent. Any conventional inert organic solvent can be utilized such as ethyl acetate, toluene, petroleum ether, or hexane. The hydrogenation of the compound of formula XI using a selective hydrogenation catalyst, produces a double bond containing a cis configuration. Therefore, selective hydrogenation of the compound of formula XI containing two acetylene linkages produces two double bonds having a cis configuration.

The compound of formula XII either as the cis or trans epoxide or as a mixture thereof can be converted to the compound of formula XIII by reacting the compound of formula XII with a cystene derivative of the formula $$\overset{NH_2}{\underset{|}{HS-CH_2-CH-COOR_4}} \qquad XVI$$

wherein $R_4$ is as above.

The reaction of the compound of formula XII with the compound of formula XVI can be carried out in the presence of an organic base. Any conventional organic base can be utilized in carrying out this reaction. Among the preferred bases are the tertiary amine bases such as the tri(lower alkyl)amines and the cyclic amines. Among the particularly preferred bases are triethyl amine, pyridine, etc. Other amine bases that can be used are monoethyl-dimethyl amine, tri(isopropyl)amine, etc. In carrying out this reaction, it is generally preferred to use an aqueous organic solvent reaction medium. As the organic solvent in this medium, any conventional water miscible organic solvent such as those mentioned herein can be utilized. In carrying out this reaction, temperature and pressure are not critical and this reaction can be carried out at room temperature and atmospheric pressure. On the other hand, higher or lower temperatures can be utilized. Generally, it is preferred to utilize a temperature of from 0° C. to 50° C.

When the compound of formula XII is the trans epoxide and the compound of formula XVI has the L or D-optical configuration, the compound of formula XIII is prepared as a mixture of the 5R,6S and 5S,6R isomers. If desired, these isomers can be separated by any conventional means. Among the preferred means is included liquid chromatography. Any of the conditions conventional in liquid chromatography separation can be utilized in carrying out this separation. On the other hand, if the cis epoxide is utilized and the compound XVI is in the L or D-configuration, the compound of formula XIII is produced as a mixture of 5S,6S, and 5R,6R. This isomeric mixture can be separated by liquid chromatography as described hereinbefore. On the other hand, if the compound of formula XII is a mixture of cis and trans epoxides, and the compound of formula XVI is racemic, the compound of formula XIII is produced as a mixture of all its isomeric forms.

The compound of formula XIII can be converted to the compound of formula I by hydrolysis. Any conventional method of ester hydrolysis such as treating with an aqueous alkali metal base can be utilized to effect this conversion. If both $R_3$ and $R_4$ are ester groups, hydrolysis will first remove $R_3$ to produce the compound of formula XIII where $R_3$ is hydrogen and $R_4$ is an ester group. Further hydrolysis will remove $R_4$. If it is desired to produce the 5S,6R isomer of formula I, then the compound of formula XIII is separated into its 5S,6R and 5R,6S isomers and the 5S,6R isomer is hydrolyzed. On the other hand, hydrolysis of the 5R,6S isomer of the compound of formula XIII will produce the compound of formula I as a 5R,6S isomer.

The compound of formula IV is produced by reacting the compound of formula XI with the compound of formula XVI in the same manner described in reacting the compound of formula XII with the compound of formula XVI to produce the compound of formula XIII. Such a reaction produces the compound of the formula

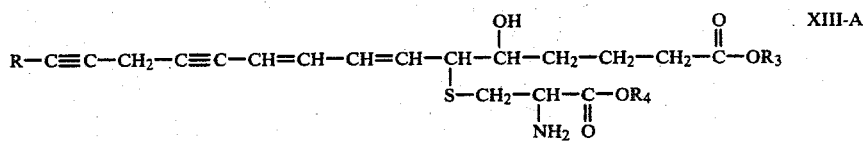

The ester groups on the compound of formula XIII-A are hydrolyzed by conventional ester hydrolysis as described hereinbefore to produce the compound of formula IV.

The compound of formula I and IV and IV-A where $R_2$ is hydrogen can be utilized in the form of their basic salts. Any of the pharmaceutically acceptable salts can be utilized in accordance with this invention. Among the preferred pharmaceutically acceptable basic salts are included the alkali metal salts such as lithium, sodium and potassium, alkaline earth metal salts such as calcium, amine salts such as the lower alkyl amine, e.g. ethylamine, and the hydroxy-substituted lower alkyl amine salt. Also preferred are the ammonium salts. Among the other salts are included salts with organic bases and amine salts such as salts with N-ethyl-piperidine, procaine, dibenzyl amine, N-dibenzylethylethylenediamine, alkylamines and salts with amino acids (e.g. salts with arginine and glycine).

The compound of formula III is produced from the epoxide of

wherein
Y is as above
by reacting this epoxide with alkali metal acetylide such as sodium acetylide to produce a compound of the formula

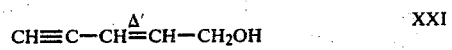

wherein
$\Delta'$ is as above.

In carrying out this invention, any conventional conditions utilized in reacting an alkali metal acetylide with a halide can be utilized. In the reaction of the halide of formula XX with an alkali metal acetylide, the double bond produced thereby is a trans double bond. On the other hand, the compound of formula XXI can be prepared with the double bond in either a cis configuration or a trans confirguration or as a mixture thereof by the following first reacting sodium acetylide with an aldehyde of the formula

to produce a compound of the formula

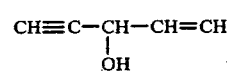

utilizing any conventional method of reacting sodium acetylide with an aldehyde. The compound of formula XXVII is subjected to conventional acid rearrangement to produce the compound of formula XXI as a mixture of cis and trans isomers. Separation of these isomers can be carried out if desired by chromatography. Any conventional method of chromatography can be utilized to effect this separation. The configuration of the double bond in the compound of formula XXI will be maintained to produce the 9-10 double bond in the compound of formula I which double bond will have the same configuration as first presented in the compound of formula XXI.

The compound of formula XXI can be etherified by any conventional means to produce the ether of formula III. Any conventional etherifying agent such as ethyl vinyl ether, etc., can be utilized to prepare the ether of formula III. Any of the conditions conventional in utilizing these ethers can be utilized in preparing the ethers of formula III.

The compound of formula II can be prepared from 2-octyn-1-ol by treatment with a halogenating agent.

The compounds of formula IV-A and salts thereof are antagonists of SRS-A and are useful agents for treating allergic reactions especially in the treatment of broncoconstriction.

Prophylactically effective amounts of compound IV-A, salts thereof or compositions containing prophylactically effective amounts of these compounds can be administered by methods well known in the art. Thus they can be administered, either singly or with other pharmaceutical agents, e.g., antagonists or mediators of anaphylaxis such as antihistamines, or anti-asthmatic steroids such as prednisone and prednisolone, orally, parenterally or by inhalation, e.g., in the form of an aerosol, micropulverized powder or nebulized solution. For oral administration they can be administered in the form of pills, tablets, capsules, e.g., in admixture with talc, starch, milk sugar or other inert ingredients, i.e. pharmaceutically acceptable carriers, or in the form of aqueous solutions, suspensions, encapsulated suspensions, gels, elixirs or aqueous alcoholic solutions, e.g., in admixture with sugar or other sweetening agents, flavorings, colorants, thickeners and other conventional pharmaceutical excipients. For parenteral administration, they can be administered in solutions or suspension, e.g., as an aqueous or peanut oil solution or suspension using excipients and carriers conventional for this mode of administration. For administration as aerosols, they can be dissolved in a suitable pharmaceutically acceptable solvent, e.g., ethyl alcohol or water or combinations of miscible solvents, and mixed with a pharmaceutically acceptable propellant. Such aerosol compositions are packaged for use in a pressurized container fitted with an aerosol valve suitable for release of the pressurized composition. Preferably, the aerosol valve is a metered valve, i.e., one, which on activation, releases a predetermined effective dose of the aerosol composition.

In practicing the method of the invention, the dose of compound IV-A of these salts to be administered and the frequency of administration will be dependent on the potency and duration of activity of the particular compound to be administered and on the route of administration, as well as the severity of the condition, age of the mammal to be treated, etc. Doses of compound IV-A contemplated for use in practicing the method of the invention are about 0.01 to about 100 mg per kilogram of body weight per day, preferably about 0.1 to about 10 mg per kilogram of body weight per day, either as a single dose or in divided doses.

The following Examples are illustrative but not limitative of the claimed invention. All temperatures are in degrees C. The ether utilized is diethyl ether. The liquid chromatography was carried out utilizing a Waters L.C. Prep 500 (preparative high performance liquid chromatography apparatus) employing two silica columns with a flow rate of 250 mL/min.

EXAMPLE 1

Liquid ammonia (1.5 L, direct from the cylinder) was saturated with acetylene (dried by passage through a dry-ice/acetone traps) was treated with sodium (50.6 g, 1 g portions) with continued passage of acetylene. The colorless mixture was then treated with epichlorohydrin (92.5 g) over 1.5 hours at −45°. After stirring the reaction mixture for a further 1.5 hours at −45°, the mixture was stirred for a further 3 hours at reflux and then quenched with ammonium chloride (75 g). The ammonia was then evaporated overnight. The residue was dissolved in water (500 mL) and extracted with ether (10×300 mL) and the combined ether extracts were dried (MgSO4) and concentrated to dryness. The residue was passed through a plug of silica gel (80 g) in a 1:1 parts by volume hexane-ethyl acetate mixture. Removal of the solvents and purification by liquid chromatography (two columns, 4:1 parts by volume hexane-ethyl acetate) gave the trans product 2-trans-penten-4-yn-1-ol (47.7 g).

EXAMPLE 2

The 2-trans-penten-4-yn-1-ol (47.7 g) was dissolved in ether (50 ml), cooled to 0° and treated with ethyl vinyl ether (50 mL). To this solution, solid p-toluene sulfonic acid (0.1 g) was added and after a slight exothermic reaction, the mixture was stirred for a further 20 min and quenched with triethylamine (2 mL). The solvents were removed in vacuo and the residue was dissolved in ether, washed with aqueous NaHCO3 solution, dried (MgSO4) and concentrated. The residue was purified by liquid chromatography (two columns, 6:1 parts by volume hexane-ethyl acetate) and distilled, bp 88°–98° (26 mmHg) to give (E)-4-methyl-3,5-dioxa-7-decen-9-yne.

EXAMPLE 3

A solution of 2-octyne-1-ol (37.8 g) in ether (150 mL) containing pyridine (3 ml) was cooled to −35° and treated with a solution of phosphorous tribromide (28.9 g) over 45 min. The mixture was then stirred at −30° for 2 hours, 3 hours at room temperature and ½ hour at 40°. The reaction mixture was then cooled to room temperature, poured onto ice and extracted with ether. The combined ether extracts were washed with aqueous NaHCO3 solution, brine and dried (MgSO4). Removal of the solvents and distillation of the residue yielded 1-bromo-2-octyne (40.9 g), bp, 106°–110° (25 mmHg).

EXAMPLE 4

A solution of ethyl magnesium bromide in tetrahydrofuran (47 mL, 1.17 M) was treated dropwise with a solution of (E)-4-methyl-3,5-dioxa-7-decen-9-yne (7.7 g) in tetrahydrofuran (10 mL). After complete addition, the mixture was heated at 60° for 45 min, cooled to room temperature, treated with anhydrous cuprous chloride (0.35 g, dried at 145° at 0.05 mmHg for 16 hours) and stirred for 10 min. The 1-bromo-2-octyne (7.23 g) in tetrahydrofuran (10 mL) was added dropwise to the above mixture (mild exothermic reaction) and after complete addition the resulting mixture was heated for 45 min at 60° C. After this time, the contents were cooled to room temperature, poured onto saturated aqueous ammonium chloride solution and extracted with ether. The combined ether extracts were washed with brine, dried (MgSO4) and concentrated. The residue was purified by liquid chromatography (two columns, 3% by volume ethyl acetate in 97% by volume hexane) to yield the product (E)-4-methyl-3,5-dioxa-7-octadecen-9,12-diyne

EXAMPLE 5

A solution of (E)-4-methyl-3,5-dioxa-7-octadecen-9,12-diyne(3.76 g) in acetone (60 mL) was treated with aqueous sulfuric acid (0.2 N, 6 mL) and left at room temperature for 3 hours. Half of the acetone was removed in vacuo and the residual solution was poured into water, extracted with ether and the combined extracts were dried (MgSO4), concentrated and purified by liquid chromatography (4:1 parts by volume hexane-ethyl acetate) to yield pure material (E)-2-tridecen-4,7-diyn-1-ol (2.5 g).

EXAMPLE 6

Pyridinium dichromate (60 g) was stirred with dichloromethane (250 mL) at 0° and treated over a period of 5 min with a solution of (E)-2-tridecen-4,7-diyn-1-ol (20 g) dissolved in dichloromethane. The cooling bath was then removed and the reaction mixture was stirred for a further 3 hours (slight exotherm; maximum temperature 33°–35°). Ether (250 mL) was then added and the solids were filtered off (through paper) and washed with more ether. The combined filtrates were concentrated and the residue was treated with hexane and filtered through celite. The filtrate was then washed with water (5×250 mL), dried (MgSO4) and concentrated to a small volume (100 ml). This solution was purified by liquid chromatography (two columns, 4:1 parts by volume hexane-ethyl acetate) to give the pure (E)-2-tridecen-4,7-diyn-1-al (11 g).

EXAMPLE 7

A solution of vinyl magnesium chloride (2.2 Molar in tetrahydrofuran 35 mL) was added to tetrahydrofuran (150 mL) and cooled to −60°. The compound (E)-2-tridecen-4,7-diyn-1-al (12.6 g) dissolved in tetrahydrofuran (50 mL) was added to the above solution over 5–10 min and the cooling bath was removed and the temperature of the reaction mixture was allowed to warm to 0° C. (20 min). Ether (200 mL) was then added followed by a saturated aqueous solution of ammonium chloride (10 mL). After the contents of the flask had been stirred for a further 15 L min, magnesium sulfate was added and after a further 30 min, the solids were filtered off and washed with ether. Removal of the solvents from the combined filtrates and purification of the residue by liquid chromatography (two columns, 10% by volume ethyl acetate in 90% by volume hexane) yielded the pure (E)-1,4-pentadecadien-6,9-diyn-3-ol (13.2 g).

EXAMPLE 8

A solution of (E)-1,4-pentadecadien-6,9-diyn-3-ol (8.5 g) in ether (200 mL) was cooled to −40° and treated over 5 min with phosphorous tribromide (3.7 mL) dissolved in ether (70 mL). The cooling bath was removed and the reaction mixture was warmed to 0° over 1 hour and then poured onto ice. The ether extract was then washed with water, sodium carbonate solution (10 mL) and dried (MgSO$_4$). Removal of the solvents and purification of the residue by liquid chromatography (two columns, hexane) gave (E,E)-1-bromo-2,4-pentadecadien-6,9-diyne as pure material (7.8 g).

EXAMPLE 9

The (E,E)-1-bromo-2,4-pentadecadien-6,9-diyne (13.8 g) was dissolved in tetrahydrothiophene (14 mL) and then treated with an aqueous methanol solution (30 mL, 9:1). The two phase system was stirred at room temperature for 40 min (clear, one phase after 5–10 min) and then concentrated, 40° at 20 mmHg and room temperature at 0.5 mm for 10 min, to give the (E,E)-2,4-pentadecadien-6,9-diyn-1-yl tetrahydrothiophenium bromide as a semi-solid (24.2 g).

EXAMPLE 10

The salt (E,E)-2,4-pentadecadien-6,9-diyn-1-yl tetrahydrothiophenium bromide (24.2 g) was dissolved in dichloromethane (100 mL) containing benzyltriethyl ammonium chloride, 0.5 g) and methyl 4-formyl butyrate (9.6 g, 1.5 Mol) and cooled to −30° with a dry ice actone bath. Cold sodium hydroxide solution (10 M, 75 mL, −5°) was rapidly added (10 sec) to the above mixture and the resulting reaction mixture was then stirred rapidly for 60 sec, the stirring was then stopped and the mixture was rapidly cooled to freeze the aqueous layer. The organic phase was decanted and the residue was washed with ether (3×100 mL, thaw and freeze). The combined organic extracts were then washed with water, dried (MgSO$_4$) and concentrated to yield the crude epoxide mixture. Purification by liquid chromatography (two deactivated columns, 10% by volume ethyl acetate and 90% by volume hexane) yielded the pure trans epoxide i.e., (R,S) (All E)-3-(1,3-tetradecadien-5,8-diyn-1-yl)-1-trans-oxiranebutanoic acid methyl ester (6.6 g), a mixed fraction (1.05 g, cis, trans) and the pure cis epoxide i.e., (R,S) (All E)-3-(1,3-tetradecadien-5,8-diyn-1-yl)-cis-oxiranebutanoic acid methyl ester (1.35 g).

To precondition the liquid chromatography columns, they were washed with 10% by volume acetic acid in 90% by volume ethyl acetate (1 L), methanol (500 mL), 10% by volume triethylamine and 90% by volume ethyl acetate (1 L), methanol (500 mL), acetone (1 L), ethyl acetate (1 L) and hexane (1 L). These columns were retained for the above separation.

EXAMPLE 11

The trans epoxide, i.e. (R,S) (All E)-3-(1,3-tetradecadien-5,8-diyn-1-yl)-1-transoxiranebutanoic acid methyl ester (1 g) was dissolved in hexane (20 mL) to yield a cloudy solution. Lindlar catalyst (poisoned, 1 g and prepared as disclosed in Organic Synthesis, Collective Volume V, Pg. 880–883) was added and the mixture was filtered through diatomaceous earth. More catalyst (1 g) was then added and the mixture was hydrogenated at room temperature and pressure. After 175 mL of hydrogen were consumed, the solids were filtered off, the filtrate was concentrated and purified by liquid chromatography (one column, 9:1 parts by volume hexane-ethyl acetate containing 2% by volume triethylamine) to yield (R,S)-(E,E,E,Z,Z)-3-(1,3,5,8-tetradecatetraen-1-yl)-1-trans-oxiranebutanoic acid methyl ester (0.5 g).

EXAMPLE 12

L-cysteine methylester hydrochloride (2.5 g) was dissolved in a water-methanol mixture (35 mL, 30:5) and the solution was adjusted to pH 8.5 with triethylamine. This solution was then added to the epoxide (R,S)-(E,E,Z,Z,)-3-(1,3,5,8-tetradecatetraen-1-yl)-1-trans-oxiranebutanoic acid methyl ester (2.5 g) and the mixture was stirred at room temperature for 4.5 hours (clear after 30 min). The solvents were then removed in vacuo and the residue was partitioned between water and ether. The ether extracts were washed with water, brine, combined and dried (MgSO$_4$). Removal of the solvents and purification of the residue by liquid chromatography (two columns, ethyl acetate) yielded the 5R,6S isomer, i.e. (5R,6S)(E,E,Z,Z,)-S-(5-hydroxy-1-methoxy-1-oxoeicosa-7,9,11,14-tetraen-6-yl)-L-cysteine methyl ester as the fastest eluting material (1.1 g), a mixture of diastereomers (0.35 g, mostly 5S,6R) and the 5S,6R isomer, i.e. (5S,6R) (E,E,Z,Z)-S-(5-hydroxy-1-methoxy-1-oxoeicosa-7,9,11,14-tetraen-6-yl)-L-cysteine methyl ester (0.9 g).

EXAMPLE 13

The 5S,6R dimethylester, i.e. (5S,6R)(E,E,Z,Z)-S-(5-hydroxy-1-methoxy-1-oxoeicosa-7,9,11,14-tetraen-6-yl)-L-cysteine methyl ester (0.3 g) was dissolved in methanol (15 mL) and treated with potassium hydroxide (150 mg) in water (1.5 mL) and left at room temperature for 90 min. Water (20 mL) was then added and the bulk of the solvents were removed in vacuo. The aqueous solution resulting from the above treatment was mixed with Dowex 50W ×4 resin (25 mL) [sulfonated polystyrene ion exchange resin in the acid form] and then poured onto a column of the same material (25 mL). The column was then washed with water until neutral and then eluted with aqueous ammonia solution (10%). As soon as the ammonia front was eluting, 150 mL was collected, treated with n-butanol (10 mL) and concentrated at 45° and 20 nm until all the n-butanol and ammonia were removed. The residual aqueous solution was then freeze-dried to yield the (5S,6R) (E,E,Z,Z)-S-(5-hydroxy-1-hydroxy-1-oxoeicosa-7,9,11,14-tetraen-6-yl)-L-cysteine mono ammonium salt as a powder (130 mg).

EXAMPLE 14

By the procedure of Example 13, the 5R,6S isomer (5R,6S) (E,E,Z,Z)-S-(5-hydroxy-1-methoxy-1-oxo-eicosa-7,9,11,14-tetraen-6-yl)-L-cysteine methyl ester is hydrolyzed to produce the (5R,6S)(E,E,Z,Z)-S-(5-hydroxy-1-hydroxy-1-oxoeicosa-7,9,11,14-tetraen-6-yl)-L-cysteine mono ammonium salt.

EXAMPLE 15

A solution of (L)-cysteine methyl ester hydrochloride (1.2 g) in aqueous methanol (20 mL; 4:1) was brought to pH 8.5 with triethylamine (3 mL) and added to the transepoxide, i.e. (R,S)(All E)-3-(1,3-tetradecadien-5,8-diyn-1-yl)-trans-oxiranebutanoic acid methyl ester (1.8 g) and stirred overnight at room temperature. Most of the methanol was removed in vacuo and the residue was partitioned between ether and water. The ether extracts were washed with water, combined, dried (MgSO$_4$) and concentrated. The crude mixture (2.8 g) was purified by liquid chromatography to give the 5S,6R (5S,6R)(E,E)-S-(5-hydroxy-1-methoxy-1-oxoeicosa-7,9-dien-11,14-diyn-6-yl)-L-cysteine methyl ester isomer (0.9 g) and its diastereomer (1.1 g) (5R,6S)-S-(5-hydroxy-1-methoxy-1-oxoeicosa-7,9-dien-11,14-diyn-6-yl)-L-cysteine.

EXAMPLE 16

(5S,6R)(E,E)-S-(5-hydroxy-1-oxo-eicosa-7,9-dien-11,14-diyn-6-yl)-L-cysteine ammonium salt The cysteine adduct (5S,6R)(E,E)-S-(5-hydroxy-1-hydroxy-1-oxo-eicosa-7,9-dien-11,14-diyn-6-yl)-L-cysteine methyl ester (0.45 g) was dissolved in a mixture of tetrahydrofuran (10 mL) and water (5 mL) containing lithium hydroxide (0.3 g) and left at room temperature for 3 hours. Water was added and the organic solvents were removed in vacuo. The residual aqueous solution of lithium salts was onto a Dowex 50 4× column (acid form 25 ml) and eluted with water and aqueous ammonium hydroxy (1 M). The ammonia eluate was freeze dried to yield (5S,6R)(E,E)-S-(5-hydroxy-1-hydroxy-1-oxo-eicosa-7,9-dien-11,14-diyn-6-yl)-L-cysteine ammonium salt.

EXAMPLE 17

By the procedure of Example 11, the cis epoxide (R,S)(E,E)-3-(1,3-tetradecadien-5,8-din-1-yl)-1-cis-oxiranebutanoic acid methyl ester is hydrogenated to the (R,S)-(E,E,Z,Z)-3-(1,3,5,8-tetradecatetraen-1-yl)-1-cis-oxiranebutanoic acid methyl ester.

EXAMPLE 18

By the procedure of Example 12, the cis isomer (R,S)-(E,E,Z,Z)-3-(1,2,5,8-tetradecatetraen-1-yl)-1-cis-oxiranebutanoic acid methyl ester is reacted with L-cysteine methyl ester hydrochloride to produce (5S,6S)(E,E,Z,Z)-S-(5-hydroxy-1-methoxy-1-oxo-eicosa-7,9,11,14-tetraen-6-yl)-L-cysteine methyl ester and (5R,6R)(E,E,Z,Z)-S-(5-hydroxy-1-methoxy-1-oxo-eicosa-7,9,11,14-tetraen-6-yl)-L-cysteine methyl ester. These products are separated in the manner of Example 12.

EXAMPLE 19

By the procedure of Example 13, the 5S,6S isomer (5S,6S) (E,E,Z,Z)-S-(5-hydroxy-1-methoxy-1-oxo-eicosa-7,9,11,14-tetraen-6-yl)-L-cysteine methyl ester is hydrolyzed to produce the (5S,6S) (E,E,Z,Z)-S-(5-hydroxy-1-hydroxy-1-oxoeicosa-7,9,11,14-tetraen-6-yl)-L-cysteine mono ammonium salt.

EXAMPLE 20

By the procedure of Example 13, the 5R,6R isomer (5R,6R) (E,E,Z,Z)-S-(5-hydroxy-1-methoxy-1-oxo-eicosa-7,9,11,14-tetraen-6-yl)-L-cysteine methyl ester is hydrolyzed to produce the (5R,6R) (E,E,Z,Z)-S-(5-hydroxy-1-hydroxy-1-oxoeicosa-7,9,11,14-tetraen-6-yl)-L-cysteine mono ammonium salt.

EXAMPLE 21

Preparation of (5S,6R) (E,E,Z,Z)-S-(5-hydroxy-1-hydroxy-1-oxo-eicosa-7,9-11,14-tetraen-6-yl)-L cysteine potassium salt (5S,6R) (E,E,Z,Z)-S-(5-hydroxy-1-hydroxy-1-oxo-eicosa-7,9,11,14-tetraen-6-yl)-L-cysteine dimethyl ester (2 g) was dissolved in methanol (50 mL) at room temperature and then treated with potassium hydroxide (1 g) dissolved in water (10 mL). After standing at room temperature for 1½ hours, water (50 mL) was added and the methanol was removed in vacuo (40° at 20 mm). The aqueous solution was then absorbed onto a Waters c.g. reverse phase column which is packed with silica bonded to a $C_{18}$ hydrocarbon, and the column was then washed well with water (5–6 column volumes). The desired material was then eluted from the adsorbent with aqueous methanol (4:1 parts by volume, methanol-water). Removal of the methanol in vacuo and freeze-drying the residual aqueous solution yielded the (5S,6R)-(E,E,Z,Z,)-S-(5-hydroxy-1-hydroxy-1-oxo-eicosa-7,9,11,14-tetraen-6-yl)-L-cysteine potassium salt as a buff colored solid.

EXAMPLE 22

The mixture of diastereomers (5R,6S) and (5S,6R) (E,E,Z,Z)-S-(5-hydroxy-1-methoxy-1-oxoeicosa-8,10,12,15-tetraen-6-yl) L-cysteine methyl ester was treated as in Example 13 to give the diastereomeric mixture of (5R,6S and 5S,6R) (E,E,Z,Z)-S-(5-hydroxy-1-hydroxy-1-oxoeicosa-7,9,11,14-tetraen-6-yl)-L-cysteine mono ammonium salts.

EXAMPLE 23

This Example is directed to natural SRS-A.

The SRS-A was obtained by challenging chopped lung fragments from actively sensitized guinea pigs with egg albumin in vitro. Male animals (200–250 g) were sensitized to egg albumin by an intraperitoneal injection of the 10 mg of antigen (egg albumin) in 1 ml of 0.9% NaCl, 28 to 45 days prior to challenge. The animals were stunned and exsanguinated and the lungs were immediately removed and placed in Tyrode's solution pH 7.4. The composition of the aqueous Tyrode's solution was (millimolar concentrations) NaCl, 136.7; KCl, 2.7; $MgCl_2$, 1.05; $NaHCO_3$, 11.9; $CaCl_2$, 1.8; $NaH_2PO_4$, 0.48; and glucose 5.5. The lung tissue was dissected from the major arteries and blood vessels, chopped into 1 mm$^3$ fragments, filtered and washed free of blood with Tyrodes solution. The chopped lung was blotted dry and suspended in Tyrodes solution to a concentration of 150 mg lung tissue per ml. The in vitro challenge was carried out by first preincubating the lung suspension at 37° C. for 5 minutes, adding the egg albumin (40 mg/ml) to the fragments and after a 10 minute challenge, separating the media containing the SRS-A from the lung tissue by filtration on filter paper.

SRS-A was assayed utilizing the procedure described by Orange and Austen, J. Immunol. 10, 105 (1969) as follows: a 1.5 cm segment of ileum was removed from male guinea pigs weighing from 250 to 300 grams. The segment of ileum was suspended in a 10 ml organ bath containing Tyrodes solution. The ileum was attached to a strain gauge transducer and contractions were recorded on a strip chart recorder. The bath contained $10^{-6}$ M atropine sulfate to block contractions which might be caused by acetylcholine and $10^{-6}$ M pyrilamine maleate to block histamine-induced contractions. The bath was maintained at 37° C. and gassed with a mixture of 95% $O_2$ and 5% $CO_2$. The concentration of SRS-A in the filtrate obtained by challenging lung tissue with egg albumin was determined by comparing the contraction solicited by a given volume of the filtrate with the contraction elicited by 5 mg of histamine (in the absence of pyrilamine maleate). One unit of SRS-A is equivalent to that quantity which will give the same contraction as this amount of histamine. The natural SRS-A used in these studies had a concentration of 270 units per ml of filtrate. After standardization, this SRS-A was stored in small aliquots at −80° C. for further use.

EXAMPLE 24

The SRS-A activity of the following materials were determined:

A = natural SRS-A prepared in Example 22;

B = (5S,6R) (E,E,Z,Z)-S-(5-hydroxy-1-hydroxy-oxo-eicosa-7,9,11,14-tetraen-6-yl-L-cysteine mono ammonium salt;

C = (5R,6S) (E,E,Z,Z)-S-(5-hydroxy-1-methoxy-1-oxoeicosa-7,9,11,14-tetraen-6-yl)-L-cysteine mono ammonium salt;

D = (5S,6R) (E,E)-S-(5-hydroxy-1-hydroxy-1-oxo-eicosa-7,9-dien-11,14-diyn-6-yl)-L-cysteine mono ammonium salt;

E = a 1 to 1 mixture of B and C;

F = (5S,6R) (E,E,Z,Z)-S-(5-hydroxy-1-hydroxy-1-oxoeicosa-7,9,11,14-tetraen-6-yl-L-cysteine mono potassium salt;

G = 5R,6S(E,E,Z,Z)-S-(5-hydroxy-1-methoxy-1-oxo-eicosa-7,9,11,14-tetraen-6-yl)-L-cysteine mono potassium salt;

H = a 1 to 1 mixture of F and G.

Varying concentrations of the above compounds were added to the guinea pig ileum bioassay system described in Example 23 to determine the maximal contractions which could be produced. The $EC_{50}$ which is reported in the table below is the concentration of test substance which gives 50% of the maximal contraction of the ileum produced by natural SRS-A (Material A). The $EC_{50}$ values were determined on several different ileum preparations. Each value is the average ± the standard error determined from "n" number of separate ileum preparations.

In the Table, S.E. means the standard error for a number of different determinations, M is the molar concentrations and n is the number of different ileums.

| Substance | $EC_{50}$(M) ± S.E. | |
|---|---|---|
| B | $5.0 \times 10^{-9} \pm 1.1$ | n = 3 |
| C | $2.8 \times 10^{-8} \pm 0.3$ | n = 2 |
| D | $1.1 \times 10^{-6} \pm 0.1$ | n = 2 |
| E | $4.2 \times 10^{-8} \pm 0.5$ | n = 5 |
| F | $4.3 \times 10^{-9} \pm 0.2$ | n = 4 |
| G | $1.2 \times 10^{-8} \pm 0.2$ | n = 2 |

EXAMPLE 25

This Example is directed to comparing the activity of the known SRS-A antagonist against natural SRS-A and against synthetic SRS-A active compounds of this invention.

In this Example, the known SRS-A antagonist is 7-[3-(4-acetyl-3-hydroxy-2-propylphenoxy)-2-hydroxypropoxy]-4-oxo-8-propyl-4H-benzopyran-2-carboxylic acid (Compound I). The natural SRS-A isomer that was utilized was obtained in Example 22. The SRS-A active compounds utilized were monoammonium salt of the 5S,6R-L-cysteine compound produced Example 20 (Compound B and Compound E).

The assay was carried out as described in Example 23. Compound I was added in varying concentrations to the assay bath (a total volume of 10 ml was maintained in the bath) and incubated with the tissue for 3 minutes. After this incubation period, an amount of the appropriate SRS-A sample (Compound A, B, or E) equivalent to that concentration which would give 50% of the maximal attainable contraction ($EC_{50}$) was added to the assay bath. The difference in the level of the contraction obtained in the absence and presence of varying concentrations of Compound I was determined. From these values, a graph was prepared of the percent inhibition of the SRS-A-induced contraction at varying concentrations of Compound I. The concentration of Compound I at which an inhibition of 50% ($IC_{50}$) could be obtained was extrapolated from this graph and is presented in the table below. This value is the average ± the standard error of "n" separate determinations.

$IC_{50}$ of Compound I against natural SRS-A = $3.7 \times 10^{-8} \pm 0.3$ (n=4).

$IC_{50}$ of Compound I against Compound B = $3.5 \times 10^{-8}$; $4.0 \times 10^{-8}$ (n=1);

$IC_{50}$ of Compound I against Compound E = $4.0 \times 10^{-8} \pm 0.2$ (n=2).

EXAMPLE 26

The procedure of Example 24 was followed except that the antagonist tested was (R,S) (All E)-3-(1,3-tetradecadien-5,8-diynyl)-trans-oxiranebutanoic acid methyl ester and the SRS-A active compound used was the synthetic component Compound E. The $IC_{50}$ was $1 \times 10^{-5}$ (n=1).

EXAMPLE 27

(R,S) (All E)-3-(1,3-Tetradecadien-5,8-diyn-1-yl)-trans-oxiranebutanoic acid methyl ester Tablets were formulated by wet granulation in accordance with the following procedure:

| | mg/tab |
|---|---|
| 1. (R,S) (All E)-3-(1,3-tetradecadien-5,8- | |

| | mg/tab | | | |
|---|---|---|---|---|
| diyn-1-yl)-trans-oxiranebutanioc-acid methyl ester | 10 | 25 | 50 | 100 |
| 2. Pregelatinized Starch | 10 | 15 | 20 | 25 |
| 3. Modified Starch | 10 | 15 | 20 | 25 |
| 4. Lactose | 158 | 177.5 | 187 | 226.5 |
| 5. Talc | 10 | 15 | 20 | 20 |
| 6. Magnesium Stearate | 2 | 2.5 | 3 | 3.5 |
| | 200 | 250 | 300 | 400 |

Procedure
1. Mix Items 1–4. Mill and remix.
2. Granulate with water. Dry overnight.
3. Mill the dry grading. Mix with Items 5 and 6 and compress.

EXAMPLE 28

(R,S)
(All-E)-3-(1,3-Tetradecadien-5,8-diyn-1-yl)-trans-oxiranebutanoic acid methyl ester Tablets are formulated by direct compression according to the following procedure:

| | mg/tab | | | |
|---|---|---|---|---|
| 1. (R,S) (All E)-3-(1,3-tetradecadien-5,8-diyn-1-yl)-trans-oxiranebutanoic-acid methyl ester | 10 | 25 | 50 | 100 |
| 2. Lactose | 108 | 147.5 | 157 | 345 |
| 3. Modified Starch | 20 | 25 | 30 | 50 |
| 4. Avicel | 40 | 50 | 60 | 100 |
| 5. Magnesium Stearate | 2 | 2.5 | 3 | 5 |
| | 180 | 250 | 300 | 600 |

Procedure
1. Mix Items 1–4 in a suitable mixer.
2. Add Item 5 and mix for five minutes. Compress on a suitable press.

EXAMPLE 29

(R,S)
(All-E)-3-(1,3-Tetradecadien-5,8-diyn-1-yl)-trans-oxiranebutanoic acid methyl ester Capsules were formulated by the following procedure:

| | mg/cap | | | |
|---|---|---|---|---|
| 1. (R,S) (All E)-3-(1,3-tetradecadien-5,8-diyn-1-yl)-trans-oxiranebutanoic-acid methyl ester | 10 | 25 | 50 | 100 |
| 2. Lactose | 145 | 143 | 168 | 187 |
| 3. Corn Starch | 40 | 40 | 60 | 80 |
| 4. Talc | 3 | 15 | 20 | 30 |
| 5. Magnesium Stearate | 2 | 2 | 2 | 3 |
| | 200 | 225 | 300 | 400 |

Procedure
1. Mix Items 1–3 in a suitable mixer.
2. Add talc and magnesium stearate and mix for five minutes.
3. Fill on suitable capsule machine.

I claim:
1. A compound of the formula

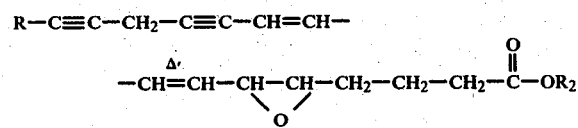

wherein
R is $CH_3-CH_2-CH_2-CH_2-CH_2$; and $R_2$ is lower alkyl and $\Delta'$ designates a trans configuration across the double bond
and pharmaceutically acceptable salts thereof where $R_2$ is hydrogen.
2. The compound of claim 1 wherein said compound is (R,S) (All E)-3-(1,3-tetradecadien-5,8-diyn-1-yl)-1-trans-oxiranebutanoic acid methyl ester.

* * * * *